(12) United States Patent
Nier et al.

(10) Patent No.: US 9,274,073 B2
(45) Date of Patent: Mar. 1, 2016

(54) METHOD AND APPARATUS FOR DETERMINING THE COMPOSITION OF MEDICAL LIQUIDS WITH REGARD TO THEIR FRACTION OF ELECTROLYTES AND NON-ELECTROLYTES

(71) Applicant: Fresenius Medical Care Deutschland GmbH, Bad Homburg (DE)

(72) Inventors: Volker Nier, Reichelsheim (DE); Andreas Wuepper, Buettelborn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 45 days.

(21) Appl. No.: 13/853,333

(22) Filed: Mar. 29, 2013

(65) Prior Publication Data
US 2013/0263650 A1   Oct. 10, 2013

Related U.S. Application Data

(60) Provisional application No. 61/620,493, filed on Apr. 5, 2012.

(30) Foreign Application Priority Data

Apr. 5, 2012  (DE) .......................... 10 2012 103 010

(51) Int. Cl.

| | |
|---|---|
| *G01N 27/06* | (2006.01) |
| *G01N 21/41* | (2006.01) |
| *A61M 1/16* | (2006.01) |
| *A61M 1/14* | (2006.01) |
| *G01N 27/08* | (2006.01) |

(52) U.S. Cl.
CPC .................. *G01N 27/06* (2013.01); *A61M 1/14* (2013.01); *A61M 1/1607* (2014.02); *A61M 1/1654* (2013.01); *G01N 21/41* (2013.01); *G01N 27/08* (2013.01)

(58) Field of Classification Search
CPC ......... G01N 27/06–27/10; B01D 61/00–61/58
USPC ................................................. 204/400–409
See application file for complete search history.

(56) References Cited

U.S. PATENT DOCUMENTS

| | | | |
|---|---|---|---|
| 5,762,769 A | 6/1998 | Gotsu et al. | |
| 2014/0018727 A1* | 1/2014 | Burbank et al. | ................ 604/28 |

FOREIGN PATENT DOCUMENTS

| | | |
|---|---|---|
| DE | 198 31 385 | 1/2000 |
| DE | 10 2004 055 032 | 8/2006 |

(Continued)

OTHER PUBLICATIONS

"Refraktometrie" In: Helm, Laszlo: "Fachlexikon ABC Messtechnik", 1985, Verlag Harri Deutsch, Thun und Frankfurk/Main, XP 002698205.

*Primary Examiner* — J. Christopher Ball
(74) *Attorney, Agent, or Firm* — Jacobson Holman, PLLC.

(57) ABSTRACT

The present invention relates to a method for determining the composition of medical liquids with regard to their fraction of electrolytes and non-electrolytes, comprising the steps of: determining at least one first physical parameter of the medical liquid for unambiguously determining the fraction of non-electrolytes in the medical liquid; simultaneously determining at least a second physical parameter of the medical liquid for determining the fraction of electrolytes in the medical liquid; and determining the fraction of electrolytes and non-electrolytes in the medical liquid based on the first and second physical parameter. The present invention further relates to an apparatus for determining the composition of medical liquids with regard to their fraction of electrolytes and non-electrolytes, comprising a first measuring apparatus (7) for measuring a first physical parameter of the medical liquid, which is unambiguously related to the non-electrolyte in medical liquid, a second measuring apparatus (8) for determining at least a second physical parameter of medical liquid, which is unambiguously related to the fraction of electrolytes in the medical liquid, and an evaluating apparatus (9) for determining the fraction of electrolytes and non-electrolytes in the medical liquid on the basis of the measured values of the first measuring apparatus (7) and the second measuring apparatus (8).

11 Claims, 4 Drawing Sheets

(56) References Cited

FOREIGN PATENT DOCUMENTS

| | | |
|---|---|---|
| EP | 1 547 629 | 6/2005 |
| JP | 60-155952 | 8/1985 |
| JP | 10-085573 | 4/1998 |
| JP | 2012-026912 | 2/2012 |
| WO | WO 96/25214 | 8/1996 |

* cited by examiner

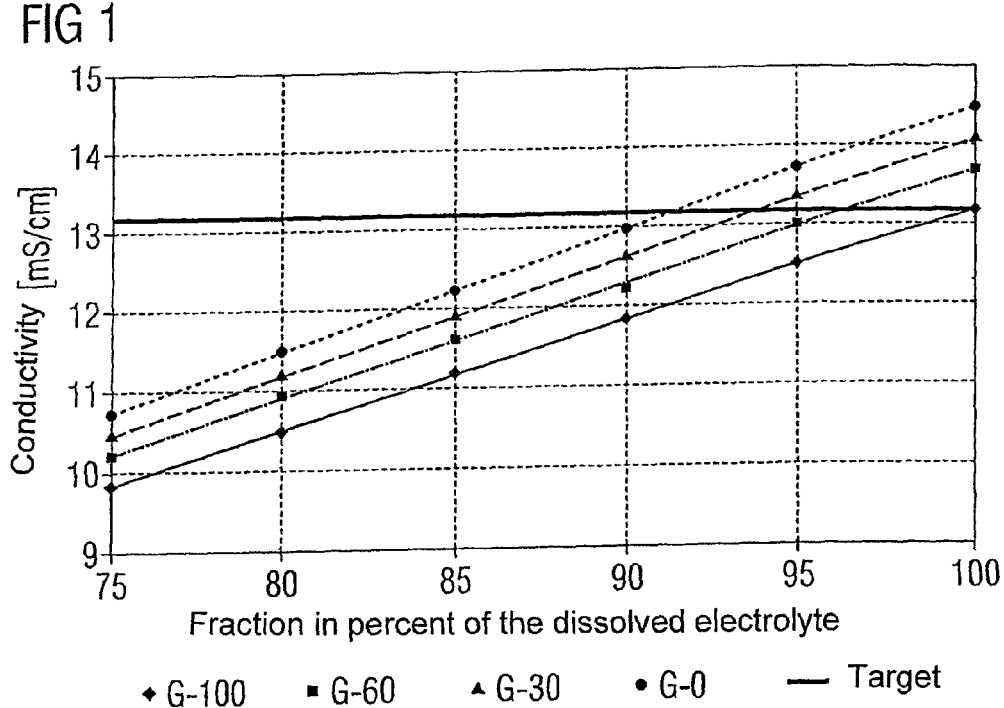
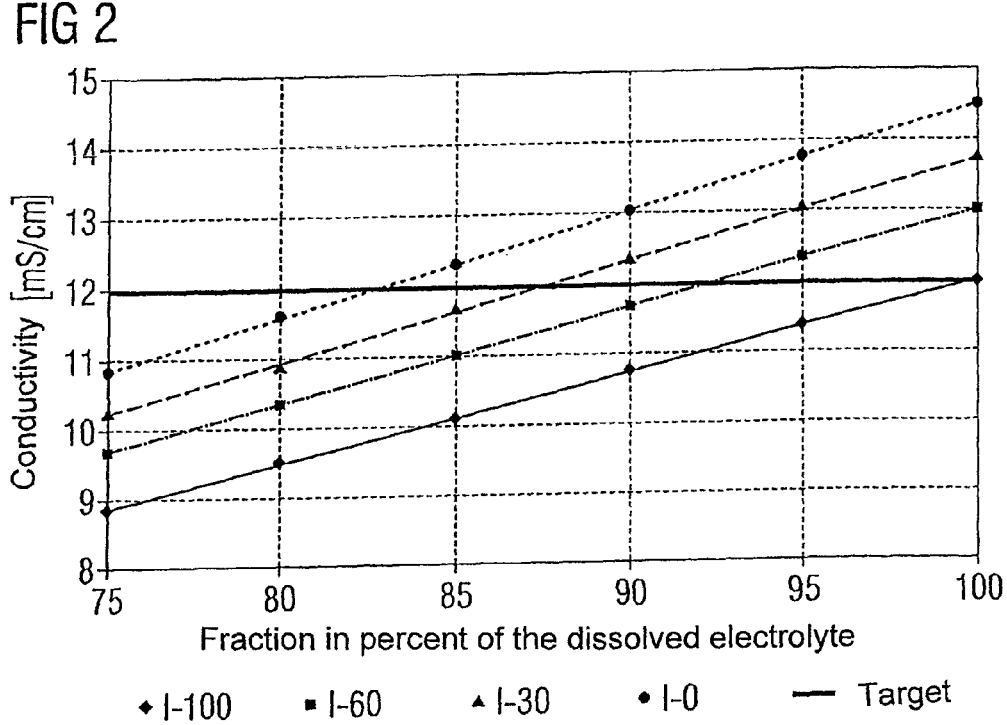

METHOD AND APPARATUS FOR DETERMINING THE COMPOSITION OF MEDICAL LIQUIDS WITH REGARD TO THEIR FRACTION OF ELECTROLYTES AND NON-ELECTROLYTES

TECHNICAL FIELD

The present invention relates to a method and an apparatus for determining the composition of medical liquids relative to their share of electrolytes and non-electrolytes. Preferably, dialysates for use in hemodialysis and peritoneal dialysis are analyzed.

PRIOR ART

In the production of medical liquids, it is often necessary to adjust certain ratios of electrolytes and non-electrolytes in the respective solution and to monitor the actual adjustment of the respective conditions.

For example, it is known in the field of dialysis, for example, in hemodialysis, hemofiltration, hemodiafiltration and peritoneal dialysis, to employ medical liquids as dialysate or as substitution liquid, which comprise both electrolytes and non-electrolytes.

Frequently, the corresponding medical liquids are mixed prior to use in the respective dialysis procedures on-line or in tanks, for example, by adding corresponding concentrates of electrolytes and non-electrolytes to water.

When mixing the corresponding concentrates with water, it must be ensured that the intended final concentrations are attained in the respective medical liquid in order to ensure a high level of patient safety. To this regard, it is known to monitor the dialysate in the dialysis machine through continuous measurement of the conductivity.

Ready-for-use solutions of the medical liquid must contain both components, namely non-electrolytes and electrolytes, at prescribed concentrations. Automatic monitoring of the provided final concentrations in the medical liquid is performed before the dialysate is used for treatment of the patient.

Because the concentrations are predetermined in the to-be-produced dialysate, its electrical conductivity is also defined. If the electric conductivity deviates from the predetermined target value during operation, then there is a malfunction of the dialysate production, and the corresponding dialysis session must be stopped or interrupted.

Furthermore, it may occur that, despite of supplying the correct amounts of electrolyte concentrate and non-electrolyte concentrate, the corresponding concentrates, e.g., if they are provided in dry form, are not completely mixed with the fluid or do not pass completely into the solution. The corresponding effect is the same, namely that the used dialysate does not show the prescribed concentration ratios.

A method for measuring the concentration of non-electrolytes in an electrolytic solution is known from U.S. Pat. No. 5,762,769, wherein the mixed electrolyte solution, which comprises at least one electrolyte and a non-electrolyte, is measured by means of an electrical conductivity measurement.

SUMMARY OF THE INVENTION

Accordingly, it is an object of the present invention to further improve the determination of the fraction of electrolyte and non-electrolyte in a medical liquid.

This object is achieved with a method having the features of claim 1. Advantageous further developments are derivable from the dependent claims.

Accordingly, the method for determining the composition of medical liquids with regard to their fraction of electrolytes and non-electrolytes comprises the steps of: determining at least one first physical parameter of the medical liquid for unambiguously determining the fraction of non-electrolytes in the medical liquid, simultaneously determining at least a second physical parameter of the medical liquid for determining the fraction of electrolytes in the medical liquid, and determining the fraction of electrolytes and non-electrolytes in the medical liquid based on the first and second physical parameter.

In that at least one first physical parameter of the medicinal solution is determined, which serves the purpose of unambiguously determining the fraction of non-electrolytes, and in that a second physical parameter of the medical liquid is simultaneously determined, which determines the fraction of electrolyte, it becomes possible to computationally eliminate the influence of the non-electrolytes from the physical parameter for the electrolyte or to take into account this parameter in determining the electrolyte concentration.

Preferably, the refractive index of the medical liquid is used as the first physical parameter for unambiguously determining the fraction of non-electrolytes in the medical liquid. The refractive index of a medical liquid and, in particular, of a dialysate is substantially independent of the concentration of electrolytes. This is particularly the case for the concentration range of electrolytes that is relevant for dialysates.

Preferably, the conductivity of the medical liquid is used as the second physical parameter of the medical liquid, which is used to determine the fraction of electrolytes. Conductivity measurements on dialysates for determining the electrolyte content in the dialysate are well known. However, by means of the method presented herein, the effect of non-electrolytes on the conductivity may be taken into account.

Preferably, the fraction of the non-electrolyte is unambiguously determined from the first physical parameter, and this determination of the fraction of the non-electrolyte is included in determining the fraction of the electrolyte on the basis of the second physical parameter, wherein, preferably, the effect of the non-electrolyte on the measurement of the second physical parameter is taken into account in determining the fraction of electrolytes.

In order to provide a distinguishing criterion, a target value or target value range for the first physical parameter and/or a target value or target value range for the second physical parameter may be predetermined, and an alarm may be triggered and/or treatment may be discontinued when the measured first physical parameter and/or the second physical parameter deviates from the respective predetermined target value or target value range. A simplification of the method can accordingly be achieved in that a medical liquid is evaluated as suitable for the particular application if both the first physical parameter, preferably the refractive index, and the second physical parameter, preferably the conductivity, respectively meet a target value or target value range. If the respective target values and target value ranges of the medical liquid are met, then it can be assumed that both the fraction for the electrolytes and the fraction for the non-electrolytes in the respective medical liquid comply with the specifications. In this way, it may be refrained from carrying out a special evaluation or a computational elimination of the effect of the non-electrolyte on the measured physical parameter of the electrolytes. The accordingly stored target values for the first and second physical parameters correspond to the values that were measured in a suitable medical liquid.

It is further preferred to measure the temperature of the medical liquid and to take into account the temperature in determining the fraction of electrolytes and non-electrolyte based on the first and second physical parameter. This may further improve the accuracy of the terms of the concentration conditions.

The above described object is further solved by an apparatus with the features of claim 8. Advantageous further developments emerge from the dependent claims.

Correspondingly, an apparatus for determining the composition of medical liquids with regard to their fraction of electrolytes and non-electrolytes is provided, which comprises a first measuring apparatus for measuring a first physical parameter of the medical liquid, which is unambiguously related to the non-electrolyte in the medical liquid. A second measuring apparatus for determining at least a second physical parameter of the medical liquid is provided, which is unambiguously related to the fraction of electrolytes in the medical liquid. Furthermore, an evaluating apparatus for determining the fraction of electrolytes and non-electrolytes in the medical liquid on the basis of the measured values of the first measuring apparatus and the second measuring apparatus is provided.

It is advantageous to monitor, in a dialysis apparatus, the dialysate used or the replacement liquid used or substitution solution by means of the method described above or by means of the apparatus described above with regard to the fractions of electrolytes and to non-electrolytes. For this purpose, it is advantageous to simplify the monitoring so that target values for both the first physical parameter, from which the concentration of non-electrolytes is unambiguously derivable, and for the second physical parameter, from which the concentration of the electrolytes may be unambiguously derivable, are provided. As long as the values to be met by the dialysate to be used are within the range of the respective target values, then the dialysate is suitable for use in the treatment of the patient. In this way, patient safety can be ensured. As soon as one of the values deviates from the target value or a target value range, the further use of the dialysate is stopped and the dialysis discontinued.

This method is suitable for hemodialysis, hemofiltration, and hemodiafiltration methods and, particularly preferably, may be used in the field of peritoneal dialysis. Here, the inflow or replacement of the dialysate is stopped when one of the measured physical parameters deviates from the target or the target range. Especially in peritoneal dialysis, high concentration levels are also obtained for the non-electrolytes so that particularly precise monitoring by means of the proposed method and the proposed apparatus may be achieved.

BRIEF DESCRIPTION OF THE FIGURES

Preferably, further embodiments and aspects of the present invention are illustrated in detail by the following description of the Figures. In the drawings:

FIG. 1 shows measurements of the conductivity of a medical liquid as a function of the fraction in percent of dissolved electrolytes at different fractions in percent of a dissolved non-electrolyte;

FIG. 2 shows measurements of the conductivity of a medical liquid as a function of the fraction in percent of the dissolved electrolyte at different fractions in percent of another dissolved non-electrolyte;

DETAILED DESCRIPTION OF PREFERRED EMBODIMENTS

Figure 3:
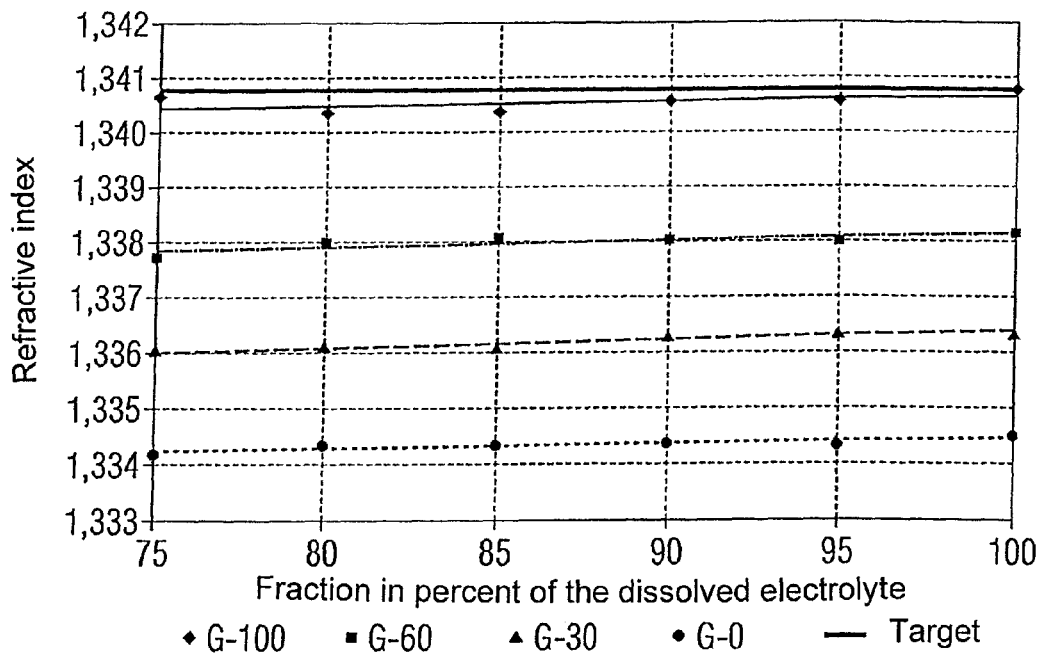
FIG. 3 shows measurements of the refractive index of a medical liquid as a function of the fraction in percent of a dissolved electrolyte at different fractions in percent of a dissolved non-electrolyte.

In the following, preferred embodiments are described with reference to the Figures. Therein, identical, similar, or equivalent elements are designated with identical reference numerals, and a repeated description of these elements is partially omitted in order to avoid redundancies in the description.

In FIGS. 1 and 2, the results of conductivity measurements on a medical liquid are shown, wherein the conductivity in mS/cm is plotted against the fraction in percent of the dissolved electrolyte. The concentrations presented in the diagrams are presented as percentage values of their respective maximum concentrations. Here, the maximum concentrations represent the values of a ready-for-use solution, which corresponds to the usual concentrations of peritoneal dialysis. The maximum concentrations are here, for example, 140 mmol/l NaCl, and 42.5 g/l glucose and 75 g/l icodextrin. The use of different concentrations reflects the eventuality that a complete dissolution of a dry concentrate cannot be achieved or that the respective dosing apparatuses, which dose the electrolytes and non-electrolytes to the medical liquid, do not work properly.

In the measurements at hand, the electrolyte was provided in the form of NaCl, wherein the presented 100% corresponds to a concentration of 140 mmol/l, i.e., the physiological correct value for NaCl in blood or in blood plasma. The remaining percentage values of the electrolyte in the measurements correspond to concentrations of 105 mmol/l (75%), 112 mmol/l (80%), 119 mmol/l (85%), 126 mmol/l (90%) and 133 mmol/l (95%).

In addition to the electrolyte NaCl, a non-electrolyte was also added into each medical liquid to be measured. In the measurement shown in FIG. 1, glucose was used as non-electrolyte. 100% glucose correspond to a concentration of 42.5 g/l, corresponding to the glucose concentration typically used in the field of peritoneal dialysis (PD). Measurements were made for 100%, 60%, 30%, and 0% added glucose portion, wherein these fractions correspond to concentrations of 42.5 g/l, 25.5 g/l, 12.75 g/l and 0 g/l glucose. In FIG. 1, the corresponding graphs are referred to as G-100, G-60, G-30, and G-0.

In FIG. 2, icodextrin was used as non-electrolyte, wherein here, a concentration of 75 g/l was used as 100%—also corresponding to the values typically used in peritoneal dialysis. The remaining concentrations are correspondingly at 45 g/l, 22.5 g/l, and 0 g/l and, analogously as in FIG. 1, are referred to as I-100, I-60, I-30, and I-0.

The conductivity in each measurement was measured using a commercially available conductivity meter, namely the "Ionometer 3" by Fresenius Medical Care.

From FIGS. 1 and 2, it can immediately be seen that the conductivity of the respective medical liquids is proportional to the electrolyte concentration. Furthermore, it can immediately be seen from the diagrams that, furthermore, the conductivity also depends on the concentration of non-electrolytes. The concentration of non-electrolytes substantially leads to a parallel shift of the respective graphs with respect to one another.

Both in FIG. 1 and in FIG. 2, a target value for the conductivity is indicated by a bold line. The target value is set so that, at correct presence of the non-electrolytes, namely at a non-electrolytes concentration of 100%, 100% of the electrolyte are in fact obtained. Accordingly, the target value is at about 13.1 mS/cm in FIG. 1 and it is at about 12 mS/cm in FIG. 2.

However, from the diagrams of FIGS. 1 and 2, it immediately follows from the curves that, at lower concentrations of the non-electrolyte, the desired electrolyte concentration of 100% is far from being attained when the target value has been reached. For example, it can be seen from FIG. 1 that, for example, at a concentration of 0% glucose, the conductivity of the medical liquid is influenced in such a way that there is only 90% of the dissolved electrolyte (corresponding to only about 126 mmol/l) when the target value of the conductivity is reached. FIG. 2 gives a similar picture. Here, for example, at 0% icodextrin, only an electrolyte concentration of about 83% is obtained when the target value of the conductivity is reached.

Accordingly, the sole measurement of the conductivity of a dialysate leads only to a correct result with regard to the electrolyte concentration if it is simultaneously ensured that the non-electrolyte concentration corresponds to the prescribed value.

Figure 4:
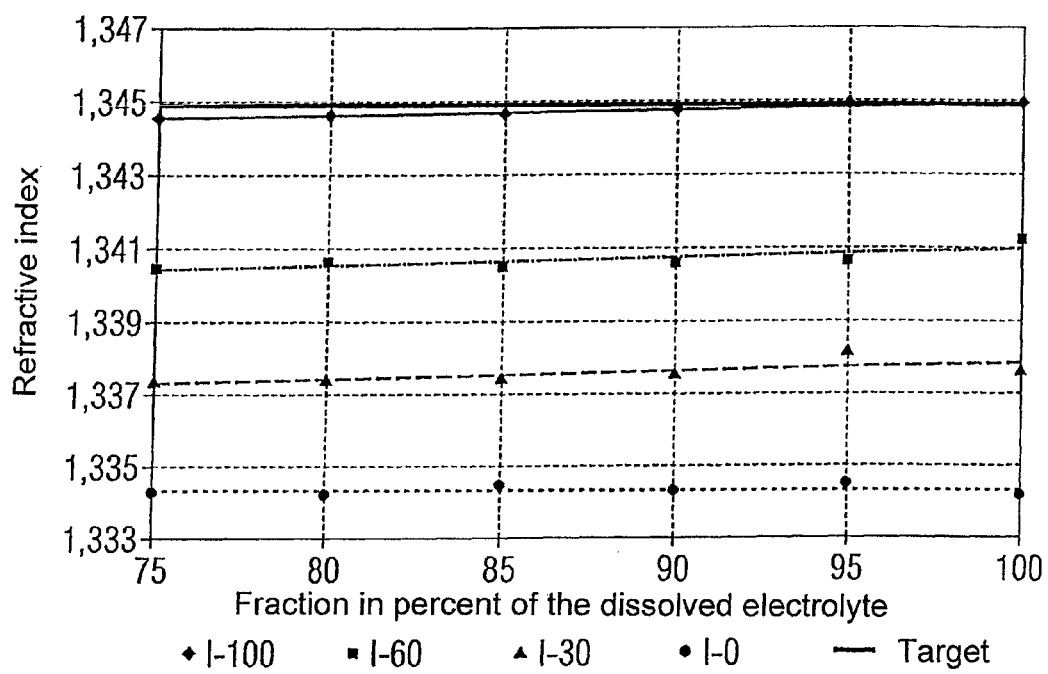
FIG. 4 shows measurements of the refractive index of a medical liquid as a function of the fraction in percent of a dissolved electrolyte at various fractions in percent of another dissolved non-electrolyte.

In FIGS. 3 and 4, measurements of the refractive index of the medical liquid have been performed in dependence of the fraction in percent of the dissolved electrolyte at various fractions in percent of the dissolved non-electrolytes. Specifically, in FIGS. 3 and 4, the same concentrations for the electrolyte (NaCl) and the non-electrolytes (glucose in FIG. 3 and icodextrin in FIG. 4) were used as in FIGS. 1 and 2. In each case, the refractive index was measured with a standard laboratory refractometer called "DR6000" by the manufacturer Krüss.

As immediately apparent from FIGS. 3 and 4 at first glance, the fraction in percent of the dissolved electrolyte is not influential for the measured refractive index in the respective tested medical liquid. On the contrary, the refractive index of the respective medical liquid is substantially independent of the electrolyte concentration—at least in the concentration range considered, which corresponds to the physiologically correct range.

The easily visible increase of the curves is substantially negligible. However, it is also derivable from FIGS. 3 and 4 that the refractive index increases with the concentration of the non-electrolyte. A target value, which, in FIGS. 3 and 4, is again indicated by the bold solid line, is here defined by the correct or prescribed concentration of the non-electrolytes.

Accordingly, by means of a measurement of the refractive index, the actual concentration of the non-electrolyte in medical liquid may be deduced independently from the dissolved electrolyte concentration. However, it is impossible to make a conclusion regarding the electrolyte concentration by means of the measurement of the refractive index.

Figure 5:
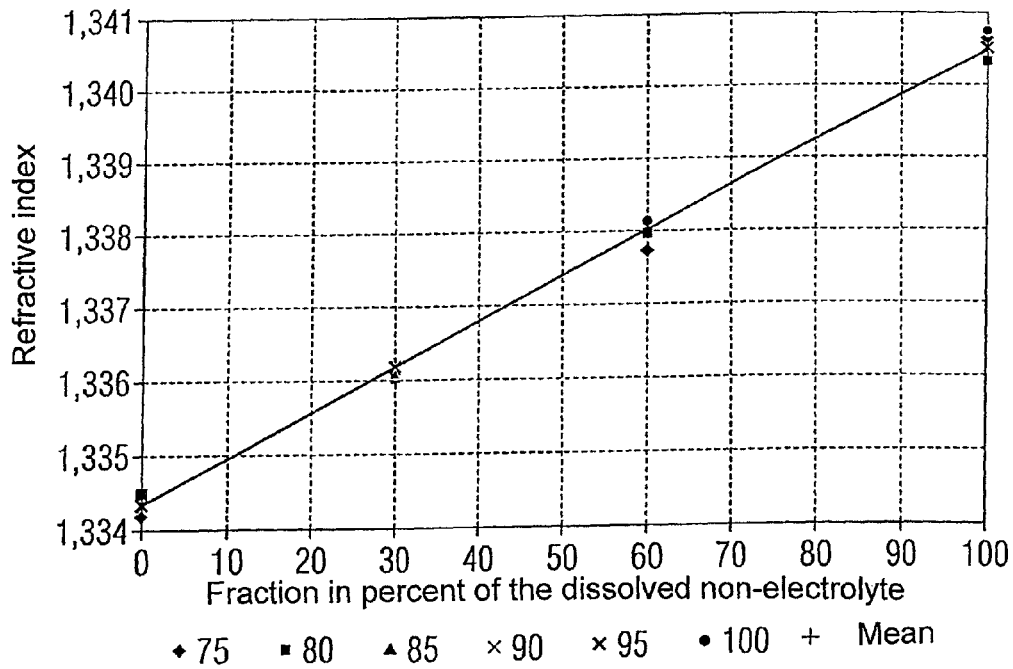
FIG. 5 shows measurements of the refractive index of a medical liquid as a function of the fraction in percent of a dissolved non-electrolyte at different fractions in percent of a dissolved electrolyte.
Figure 6:
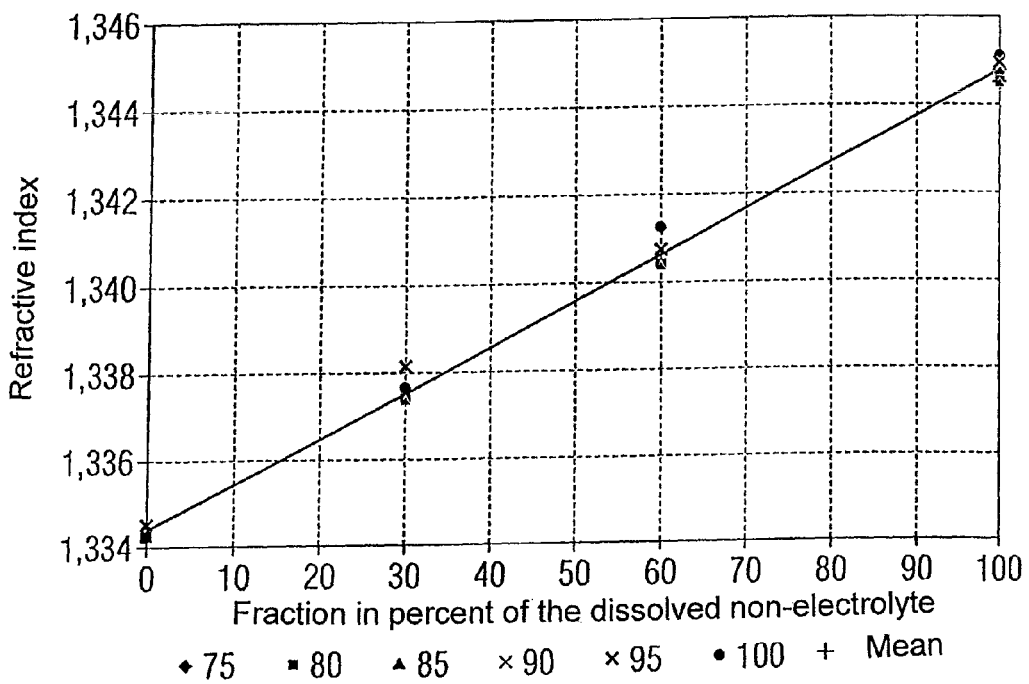
FIG. 6 shows measurements of the refractive index of a medical liquid as a function of the fraction in percent of another dissolved non-electrolyte at different fractions in percent of a dissolved electrolyte.

In FIGS. 5 and 6, further measurements of the refractive index are shown at different fractions in percent of the electrolyte, this time, as a function of the fraction in percent of dissolved non-electrolytes in the medical liquid. For these measurements too, the same solutions as in the above-mentioned measurements were used, wherein glucose is in turn used as non-electrolyte in FIG. 5 and icodextrin in FIG. 6. The electrolyte in both cases was NaCl.

It is immediately clear from FIGS. 5 and 6 that there is a proportional relationship between the fraction in percent of the dissolved non-electrolyte and the refractive index, whereas the concentration of electrolytes—at least in the physiologically relevant concentration range—does not affect the measurement of the refractive index.

According to the proposed method, a determination of at least one first physical parameter of the medical liquid, which may be used to unambiguously determine the fraction of non-electrolytes, is correspondingly carried out. In this determination, the first physical parameter preferably is the refractive index, which, as is apparent for example from the FIGS. 3 to 6, in fact allows drawing an unambiguous conclusion on the concentrations of the non-electrolytes in the medical liquid.

By means of the determination of the refractive index, the fraction of non-electrolytes may directly be derived.

Simultaneously to determining the refractive index, a second measurement is performed, which is used for determining a second physical parameter, which permits determining the fraction of electrolytes. Preferably, the conductivity is measured here. As is apparent, for example, from FIGS. 1 and 2, the concentration of the electrolyte may be derived having knowledge of the concentration of non-electrolytes through the conductivity measurement.

In this way, the influence of non-electrolytes on the determination of the concentration of the electrolyte may be computationally eliminated. According to an alternative, the respective values for the concentration of the electrolyte are read from a stored table/database, wherein, here, conductivity values for certain concentrations of electrolytes are stored for different concentrations of the non-electrolyte.

On the basis of the two measured physical parameters, namely the refractive index and the conductivity, it may accordingly be determined whether the fraction of electrolyte and of non-electrolyte in the considered medical liquid corresponds to the respective predetermined value. This determination is preferably carried out automatically.

Accordingly, in contrast to the sole measurement of the conductivity, monitoring the composition of the medical solution may be achieved with a combined measurement of the two quantities.

When used in a medical device, such as a dialysis apparatus, it may be determined whether the non-electrolyte concentration is in a particular target range through the determination of the refractive index of the medical liquid. If the refractive index is in this target range, then this indicates that the used medical liquid has the desired non-electrolyte concentration. The remaining question regarding the electrolyte concentration is then unambiguously determined through the conductivity measurement.

Accordingly, in this constellation, in particular, when a first concentrate, for example, in dry form or in solution form, which comprises the non-electrolyte, and a second concentrate, also in solution form or in dry form, which comprises the electrolyte, is mixed into the medical liquid, it may be ensured that both the concentration of non-electrolytes through the measurement of refractive index and the concentration of the electrolyte through the measurement of the conductivity are in the target value range.

By unambiguously determining the correct solution composition, an increased patient safety may accordingly be ensured.

One possibility for easily monitoring a medical apparatus for the preparation of medical liquids is then provided by means of storing target ranges for the refractive index and for the conductivity of the medical liquid. If the measured values of the refractive index and the conductivity drift away from the predetermined target value ranges, then the treatment is terminated or interrupted.

In a preferred variant, the temperature of the respective measured medical liquid is additionally measured in order to take into account, in the determination of whether the medical liquid moves in the predetermined range, variations of the measured values of the refractive index and the conductivity that result from temperature variations.

However, on the basis of the carried-out measurements, it is also possible to conclude on a potential error factor, for example, on too low dosing of the non-electrolyte or the electrolyte.

By means of a corresponding analysis, it is in fact possible to determine both the concentration of the electrolyte and the concentration of non-electrolytes, if the corresponding data is present.

As is apparent from FIGS. 5 and 6, the refractive index is linearly dependent on the concentration of non-electrolytes in the medical liquid. This results in:

$$RI = RI_0 + x_{NE} m_{RI} \quad (1)$$

Herein, RI is the refractive index of the medical liquid, $RI_0$ a zero offset, which is determined by the used solution, $x_{NE}$ the concentration or the degree of dissolution of non-electrolytes in the medical liquid, and $m_{RI}$ the slope of each curve in the Figures.

From this it is possible to determine the degree of dissolution or the concentration of the non-electrolyte to be:

$$x_{NE} = (RI - RI_0)/m_{RI} \quad (2)$$

Also, the conductivity can accordingly be linearized, as is apparent, for example, from FIGS. 1 and 2, because a linear dependence exists between the electrolyte concentration and the non-electrolyte concentration on the one side and the conductivity on the other side. For an accurate determination, however, it is to be kept in mind that the respective straight lines in FIGS. 1 and 2 are not shifted exactly in parallel to each other, but have slightly different slopes. Therefore, the following applies to the conductivity:

$$LF = LF_0(x_{NE}) + x_E \times m_{LF}(x_{NE}) \quad (3)$$

Here, LF is the conductivity of the medical liquid, $LF_0(x_{NE})$ the zero offset caused by the non-electrolyte, $x_E$ the concentration or the degree of dissolution of the electrolyte, and $m_{LF}(x_{NE})$ the slope of the measured curve, which depends on the concentration of the non-electrolyte.

This thus yields for the concentration of the electrolyte or its degree of dissolution:

$$x_E = (LF - LF_0)(x_{LME})/m_{LF}(x_{ME}) \quad (4)$$

However, because the effect of non-electrolyte concentration on the slope of the conductivity is not very big—or negligible—, an average slope is used for the sake of a simplified calculation:

$$x_E = (LF - LF_0)(x_{ME})/m_{LF} \quad (5)$$

From this, the corresponding estimate results, both for the degree of dissolution or the concentration of non-electrolytes (cf. equation (2)) and for the concentration or the degree of dissolution of the electrolyte (cf. equation (5)).

Figure 7:
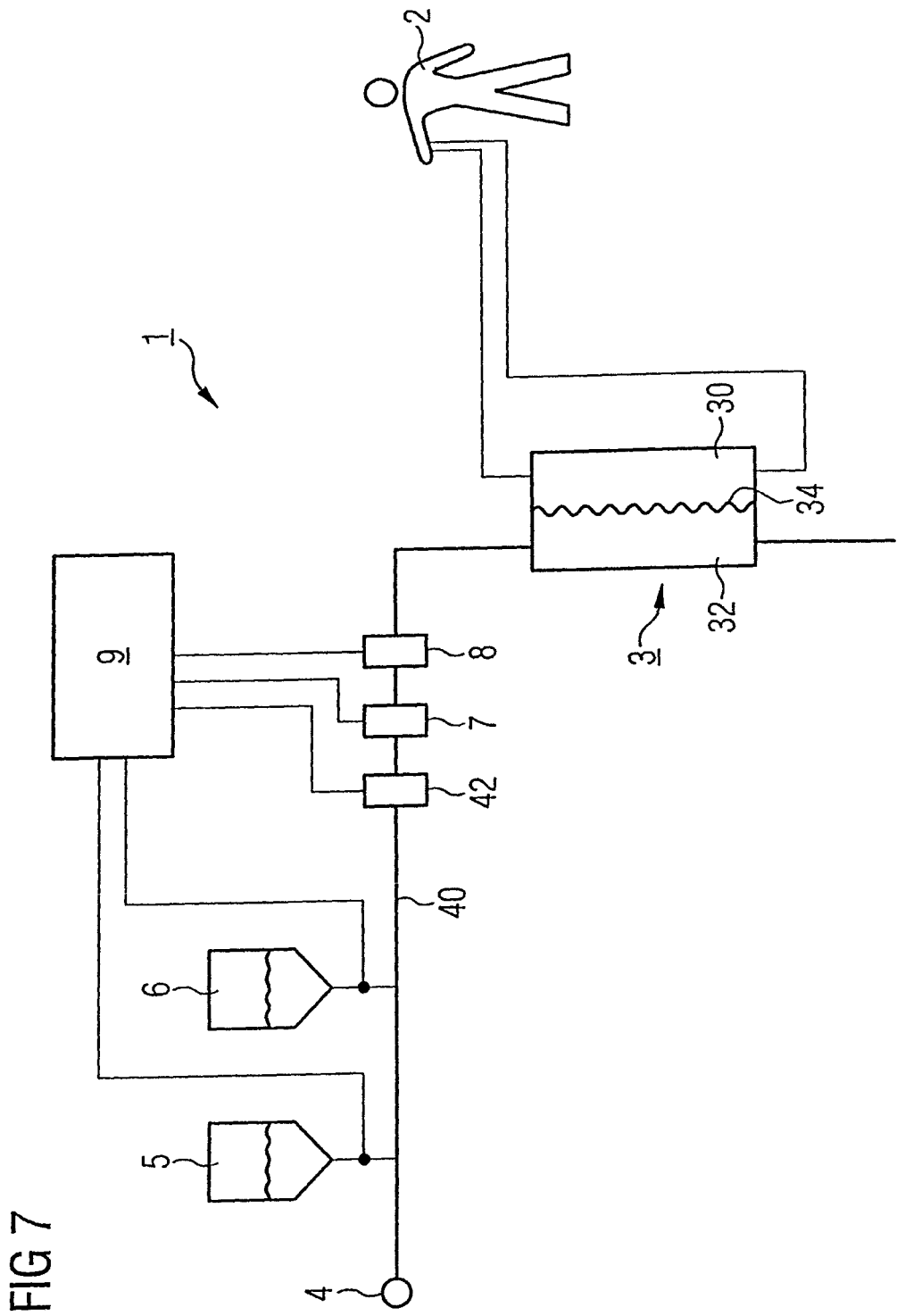
FIG. 7 shows the schematic design of a hemodialysis apparatus.

FIG. 7 schematically shows a hemodialysis apparatus 1, by means of which a schematically indicated patient 2 is dialyzed. A dialyzer 3 is provided, which has a patient side 30 and a dialysate side 32, wherein the two chambers are separated from one another by the dialysis membrane 34.

The dialysate is prepared online, and water from a water connection 4 is mixed with a concentrated electrolyte from a corresponding electrolyte dosing apparatus 5 and a non-electrolyte concentrate from a corresponding non-electrolyte dosing apparatus 6. The electrolyte dosing apparatus 5 and the non-electrolyte dosing apparatus 6 are each controlled automatically—for example via an evaluation apparatus 9—and correspondingly dose such an amount of electrolyte concentrate and non-electrolyte concentrate into the water that the required concentrations of electrolyte and to non-electrolyte are obtained in the resulting dialysate.

A refractive index sensor 7 is provided subsequent to the two metering devices 5, 6 in the line 40, through which the dialysate is transported. The refractive index sensor 7 is provided to determine the refractive index of the dialysate so that the concentration of the non-electrolyte in the dialysate is directly derivable by means thereof. This evaluation is achieved via the control device 9, to which the corresponding signals of the refractive index sensor 7 are passed. The corresponding mathematical relationships have already been explained above. In particular, there is a linear relationship between the refractive index and the concentration of the non-electrolyte in the dialysate.

Furthermore, a conductivity sensor 8 is provided, by means of which the conductivity of the produced dialysate may be measured. As already described above, the concentration of the electrolyte can be derived from the conductivity of the dialysate if the concentration of the non-electrolyte is taken into account. Because the concentration of the non-electrolyte is, however, already known based on the measurement of the refractive index sensor 7, the concentration of the electrolyte in the dialysate can accordingly be derived in the evaluation apparatus 9.

In a preferred variant, a temperature sensor 42 is also provided in line 40, by means of which the temperature of the dialysate may be determined, since the refractive index and/or the conductivity of the dialysate may change with temperature.

The hemodialysis apparatus presented in FIG. 7 is shown only schematically. The skilled person immediately recognizes that the described, simultaneous measurement of the refractive index and the conductivity may be used not only in hemodialysis apparatuses, but also in hemofiltration apparatuses for monitoring the substitution solution, in hemodiafiltration apparatuses for monitoring the concentrations of the dialysate and for monitoring the substitution solution, as well as in peritoneal dialysis apparatuses for monitoring the dialysate.

The present invention may also be used for monitoring or determining the fractions or concentrations of electrolytes and non-electrolytes in medical liquids in other medical contexts.

The medical liquid, in particular, the dialysate, may be prepared in different ways. In particular, they may be prepared by mixing dry concentrate with a starting solution, such as water, wherein either the electrolytes and the nonelectrolytes are already premixed in the dry concentrate, or two different dry concentrates are mixed in the desired ratio in such a way that the electrolytes are provided in the one dry concentrate and the non-electrolytes are provided in the other dry concentrate. Further, mixing the medical solution may also be performed by adding solution concentrates, namely either combined solution concentrates or separate solution concentrates. Combining a dry concentrate, for example, for the electrolytes, with a solution concentrate, for example, for non-electrolytes, or vice versa, may also be feasible. Mixing dilute solutions, in which electrolytes and non-electrolytes are separated, may also lead to a medical liquid.

In FIG. 7, in addition to monitoring the concentrations of the electrolytes or the non-electrolytes by means of the refractive index measurement, conductivity measurement, and, if applicable, temperature measurement, it is also possible to influence the concentrations by means of a loop control circuit. For this purpose, the evaluation apparatus 9 influences the corresponding electrolyte dosing apparatus 5 or the corresponding non-electrolyte dosing apparatus 6 when the measured concentrations of the electrolyte or of the non-electrolyte deviates from to a desired concentration. If, for example, the concentration of non-electrolytes is too low, then the non-electrolyte dosing apparatus 6 is instructed to provide a higher amount of non-electrolyte concentrate. The same can also be carried out for the electrolyte dosing apparatus 5.

In a variant, target values for the electrolyte concentration and the non-electrolyte concentration or target value ranges for the respective concentrations are stored in the evaluation apparatus 9. If the measured values for the electrolyte concentrations and the non-electrolyte concentrations are outside of the target value ranges, then the dialysis is suspended or cancelled.

The dependence of the refractive index on the non-electrolyte concentration is relatively small so that the present invention is particularly suitable for the preparation of solutions or medical liquids with high non-electrolyte concentrations. The present method or the present apparatus is therefore particularly suitable for monitoring the production of medical liquids or dialysates suitable for peritoneal dialysis because these dialysates, having 42.5 g/l glucose and 75 g/l icodextrin, show a high non-electrolyte concentration.

When using the method or the device for hemodialysis, the effect of refractive index measurement for non-electrolytes is relatively low because usually concentrations of glucose in the range of 1 g/l are used in such dialysates. These relatively low concentrations, however, have merely a minor effect on the conductivity so that the conventional dialysis can get along with conductivity measurements alone. On the contrary, the present apparatus or the present method can be used particularly advantageously when employing dialysis methods or dialysis apparatus that use higher concentrations of non-electrolytes, for example, when admixing glucose for specific glucose profiles or for a bolus of glucose.

Where applicable, all individual features that are illustrated in the various embodiments may be combined and/replaced with each other without departing from the scope of the invention.

LIST OF REFERENCE NUMERALS

1 hemodialysis apparatus
2 patient
3 dialyzer
30 patient side
32 dialysate side
34 membrane
4 water connection
40 line
42 temperature sensor
5 electrolyte dosing apparatus
6 non-electrolyte dosing apparatus
7 refractive index sensor
8 conductivity sensor
9 evaluation apparatus

The invention claimed is:

1. A method for determining the composition of medical liquids with regard to their fraction of electrolytes and non-electrolytes, comprising the steps of:
   measuring at least one first physical parameter of the medical liquid for unambiguously determining the fraction of non-electrolytes in the medical liquid;
   measuring at least a second physical parameter of the medical liquid; and
   determining the fraction of electrolytes in the medical liquid based on the measured second physical parameter taking into account the effect of the unambiguously determined non-electrolyte fraction on measurement of the second physical parameter.

2. The method according to claim 1, wherein the first physical parameter is the refractive index of the medical liquid.

3. The method according to claim 1, wherein the second physical parameter is the electrical conductivity of the medical liquid.

4. The method according to claim 1, wherein a target value or target value range for the first physical parameter and/or a target value or target value range for the second physical parameter is predetermined, and an alarm is triggered and/or treatment is discontinued when the measured first physical parameter and/or the second physical parameter deviates from the respective predetermined target value or target value range.

5. A method according to claim 1, wherein the temperature of the medical liquid is measured and the temperature is taken into account in determining the fraction of electrolytes and non-electrolyte based on the first and second physical parameter.

6. A method for operating a dialysis apparatus, wherein the fraction of electrolytes and non-electrolytes in the dialysate is determined by the method according to claim 1.

7. An apparatus for determining the composition of medical liquids with regard to their fraction of electrolytes and nonelectrolytes, which comprises
   a first measuring apparatus (7) configured for measuring a first physical parameter of the medical liquid, which is unambiguously related to the non-electrolyte in the medical liquid;
   a second measuring apparatus (8) configured for determining at least a second physical parameter of the medical liquid, which is unambiguously related to the fraction of electrolytes in the medical liquid; and
   an evaluating apparatus (9) configured for determining the fraction of electrolytes in the medical liquid on the basis of the measured values of the first measuring apparatus (7) and the second measuring apparatus (8).

8. An apparatus according to claim 7, wherein the first physical parameter is the refractive index of the medical liquid.

9. The apparatus of claim 7, wherein the second physical parameter is the electrical conductivity of the medical liquid.

10. Apparatus according to claim 7 further comprising a temperature sensor (42) configured for measuring the temperature of the medical liquid.

11. Dialysis apparatus, hemodialysis apparatus, hemofiltration apparatus, hemodiafiltration apparatus or peritoneal dialysis apparatus, comprising an apparatus according to claim 7 for determining the fraction of electrolytes and non-electrolytes in the dialysate and/or the substitution solution.

\* \* \* \* \*